(12) United States Patent
Retzlaff

(10) Patent No.: US 10,162,189 B2
(45) Date of Patent: Dec. 25, 2018

(54) DEVICE, SYSTEM AND METHOD FOR THE VISUAL ALIGNMENT OF A PIPETTOR TIP AND A REFERENCE POINT MARKER

(71) Applicant: STRATEC Biomedical AG, Birkenfeld (DE)

(72) Inventor: Ruediger Retzlaff, Neuenbuerg (DE)

(73) Assignee: STRATEC Biomedical AG, Birkenfeld (DE)

( * ) Notice: Subject to any disclaimer, the term of this patent is extended or adjusted under 35 U.S.C. 154(b) by 0 days.

(21) Appl. No.: 15/074,177

(22) Filed: Mar. 18, 2016

(65) Prior Publication Data

US 2016/0274366 A1 Sep. 22, 2016

(30) Foreign Application Priority Data

Mar. 18, 2015 (GB) .................................. 1504582.6

(51) Int. Cl.
*G02B 27/62* (2006.01)
*G01N 35/10* (2006.01)

(52) U.S. Cl.
CPC .......... *G02B 27/62* (2013.01); *G01N 35/1011* (2013.01)

(58) Field of Classification Search
CPC ............................. G02B 27/62; G01N 35/1011
USPC ....................................................... 73/864.25
See application file for complete search history.

(56) References Cited

U.S. PATENT DOCUMENTS

| 4,608,494 A * | 8/1986 | Kobayashi ............ H01L 21/681 250/458.1 |
| 4,944,922 A * | 7/1990 | Hayashi ............... G01N 35/1009 356/624 |
| 5,195,234 A | 3/1993 | Pine et al. |
| 5,590,456 A * | 1/1997 | Armington ............ G02B 6/4221 29/721 |
| 5,629,767 A * | 5/1997 | Tchejeyan ............... F41G 3/326 33/348 |
| 5,772,327 A * | 6/1998 | Zheng .................. G02B 6/2551 374/160 |
| 6,203,082 B1 * | 3/2001 | Bendat ................. B25J 15/0616 29/743 |
| 6,206,583 B1 * | 3/2001 | Hishikawa ........... G02B 6/2551 385/96 |
| 6,359,694 B1 | 3/2002 | Redele |
| 6,389,688 B1 * | 5/2002 | Srivastava ............ H01L 21/681 29/720 |

(Continued)

FOREIGN PATENT DOCUMENTS

WO 2005/103656 A1 11/2005

*Primary Examiner* — Lisa Caputo
*Assistant Examiner* — Nathaniel T Woodward
(74) *Attorney, Agent, or Firm* — 24IP Law Group; Timothy R DeWitt

(57) ABSTRACT

The present invention is directed to a device, system and method for the visual alignment of a pipettor tip and a reference point marker. The invention also relates to a use of the device. The device comprises a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other.

12 Claims, 3 Drawing Sheets

(56) References Cited

U.S. PATENT DOCUMENTS

| | | | | |
|---|---|---|---|---|
| 6,435,808 B1 * | 8/2002 | Araya | ................ | H05K 13/0413 |
| | | | | 294/185 |
| 6,573,987 B2 * | 6/2003 | Shires | .................... | G01N 21/88 |
| | | | | 348/126 |
| 6,781,775 B2 * | 8/2004 | Bendat | ..................... | G02B 5/04 |
| | | | | 356/399 |
| 7,061,522 B1 * | 6/2006 | Kojima | ................. | G01M 11/37 |
| | | | | 348/47 |
| 7,591,597 B2 * | 9/2009 | Pasqualini | ............. | H05K 13/08 |
| | | | | 396/428 |
| 2009/0129731 A1 * | 5/2009 | Contag | ................ | G01J 5/0003 |
| | | | | 385/96 |
| 2012/0065912 A1 | 3/2012 | Corkan et al. | | |
| 2013/0280143 A1 * | 10/2013 | Zucchelli | ............... | B25J 9/1697 |
| | | | | 422/501 |

\* cited by examiner

DEVICE, SYSTEM AND METHOD FOR THE VISUAL ALIGNMENT OF A PIPETTOR TIP AND A REFERENCE POINT MARKER

CROSS-REFERENCE TO RELATED APPLICATIONS

The present application claims priority to British Patent Application No. GB 1504582.6 filed on Mar. 18, 2015. The aforementioned application is herby incorporated by reference in its entirety.

BACKGROUND OF THE INVENTION

Field of the Invention

The present invention is directed to a device, system and method for the visual alignment of a pipettor tip and a reference point marker. The invention also relates to a use of the device.

Brief Description of the Related Art

In order to precisely access positions in an automated analyser system, such as a robotic pipetting system, the location of the positions has to be trained at least on a first set-up of the pipetting system. Usually the process has to be repeated upon any intervention that can lead to a shift of positions.

The current standard procedure is to access a number of reference point marker positions with the robotic pipetting system either via manual movement commands or via automated detection of the reference point marker position by measuring the capacity between pipettor tip or pipettor needle and reference point marker or by measuring the motor current of the z-axis drive to detect a collision of pipettor needle and reference point marker.

In case of manual movement, the analyser system and the reference point marker positions are aligned by the operator usually by visual means.

By determining some (usually 2 or 3) reference point marker coordinates in analyser system coordinates it is possible to interpolate coordinates in an area framed by the reference point markers.

The pipettor tip and the reference point marker have to be aligned in three dimensions, x-, y- and z-direction.

U.S. Pat. No. 5,195,234 discloses an apparatus for visually aligning parts for placement using one camera that comprises a device for picking and placing a part on an object, a device for moving and removing optics into and out of a work envelope having the object, a device for locating landmarks on the object within the work envelope, and a device for aligning the part with the landmark in the work envelope.

In U.S. Patent Application Publication No. 2012/065912 A1 an apparatus is disclosed that includes a calibration member, an imaging device and a proximity sensor. The calibration member is configured to be removably coupled to a deck of a liquid handling system. The calibration member has an alignment portion configured to matingly engage a portion of the deck such that a position of the calibration member is fixed with respect to the deck. The imaging device is coupled to the calibration member such that an axis of a lens of the imaging device intersects the deck at a first predetermined location relative to a deck reference point in at least a first dimension and a second dimension. The proximity sensor is coupled to the calibration member such that a calibration reference point on the proximity sensor is at a second predetermined location relative to the deck reference point in a third dimension.

U.S. Pat. No. 6,359,694 B1 a device and method for detecting the position of components and/or for checking the position of terminals of components is described. An insertion head with such a device for detecting the position of components and/or for checking the position of terminals of components is further disclosed, the components are illuminated with vertically incident light, with multi-directional, obliquely incident light, and with horizontally incident light, so that the side surfaces of the components, and thus the projecting terminals as well are sufficiently illuminated. For the horizontal illumination, a light deflection element is employed wherein light is emitted by a light source into the light deflection element, is reflected at a first outer wall of the light deflection element, and is directed into an opening of the light deflection element in which the component is disposed.

WO 2005/103656 A1 describes a multiple surface viewer that provides views of several surfaces of an object. Light is reflected onto a beam splitter which reflects it towards a plurality of reflectors and onto a front surface of an object under inspection. The reflectors reflect the light onto side surfaces of the object. The image of the front surface is reflected back to the beam splitter, as are images of the side surfaces, via the reflectors. The various images pass through the beam splitter to a focusing lens, which focuses the composite image onto an image capture device. The multiple surface viewer captures images of multiple views of an object, without needing to rotate or flip the object The visual alignment of the state of the art of the pipettor tip and the reference point marker has a number of disadvantages:
1) It is difficult for the user to align the pipettor tip and the reference point marker in a precise manner because the reference point markers are at different positions inside the analyser system.
2) Usually, at least one dimension (x, y or z) is not visible for the user due to neighbouring modules which are covering the reference point marker.
3) The user usually has to move to different positions within the analyser system in order to visually align the pipettor tip and the reference point marker in the different dimensions.

SUMMARY OF THE INVENTION

It is thus an object of the present invention to provide a device, system and method for the visual alignment of a pipettor tip and a reference point marker, which allows a precise and easy visual alignment of the pipettor tip and the reference point marker.

The present invention provides a device for the visual alignment of a pipettor tip and a reference point marker in x-, y- and z-direction comprising a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other.

Mirror, lenses and windows of a device of the instant disclosure can be arranged in an L-shape.

It is further intended that two first windows or two second windows or one first window and one second window are each combined to one window, wherein two lenses may be combined to one lens.

A further object of the instant disclosure is a system for the visual alignment of a pipettor tip and a reference point marker in x-, y- and z-direction comprising a device comprising a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other and further comprising a camera and a user interface.

The user interface can be a computer monitor.

Another object of the instant disclosure is a system for the visual alignment of a pipettor tip and a reference point marker in x-, y- and z-direction comprising a device comprising a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other and further comprising a camera and an instrument control unit.

A method for the visual alignment of a pipettor tip and a reference point marker in x-, y- and z-direction is a further object of the instant invention. The method comprises the steps of placing a device comprising a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other so that a pipettor tip and a reference point marker are visible in the two first windows, moving the pipettor tip relative to the reference point marker in a first movement in a xz-plane and magnifying the first movement by a lens so that the magnified first movement is visible through one of the second windows, moving the pipettor tip relative to the reference point marker in a second movement in a yz-plane, reflecting the second movement by a mirror, magnifying the reflected second movement by a lens so that the reflected magnified second movement is visible through another one of the second windows, aligning the position of the pipettor tip to the position of the reference point marker in x-, y- and z-direction.

The first movement within the method steps may be in the yz-plane and the second movement may be in the xz-plane.

It is further intended that a camera acquires the first and the second movement and the first and the second movement are visible on a user interface, wherein the user interface can be a computer monitor.

Alternatively, a camera may acquire the first and the second movement and the alignment is performed by an instrument control unit using image processing algorithms.

Finally, a use of a device of the instant disclosure may comprise a mirror and two lenses inside the device and four windows, wherein two first windows are perpendicular to each other, the mirror is arranged behind one of the two first windows, the two lenses are each arranged behind two second windows, one of the first windows and one of the second windows are arranged parallel to each other, and one of the first windows and one of the second windows are arranged perpendicular to each other for the visual alignment of a pipettor tip and a reference point marker in x-, y- and z-direction Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

For a more complete understanding of the present invention and the advantages thereof, reference is now made to the following description and the accompanying drawings, in which.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1:
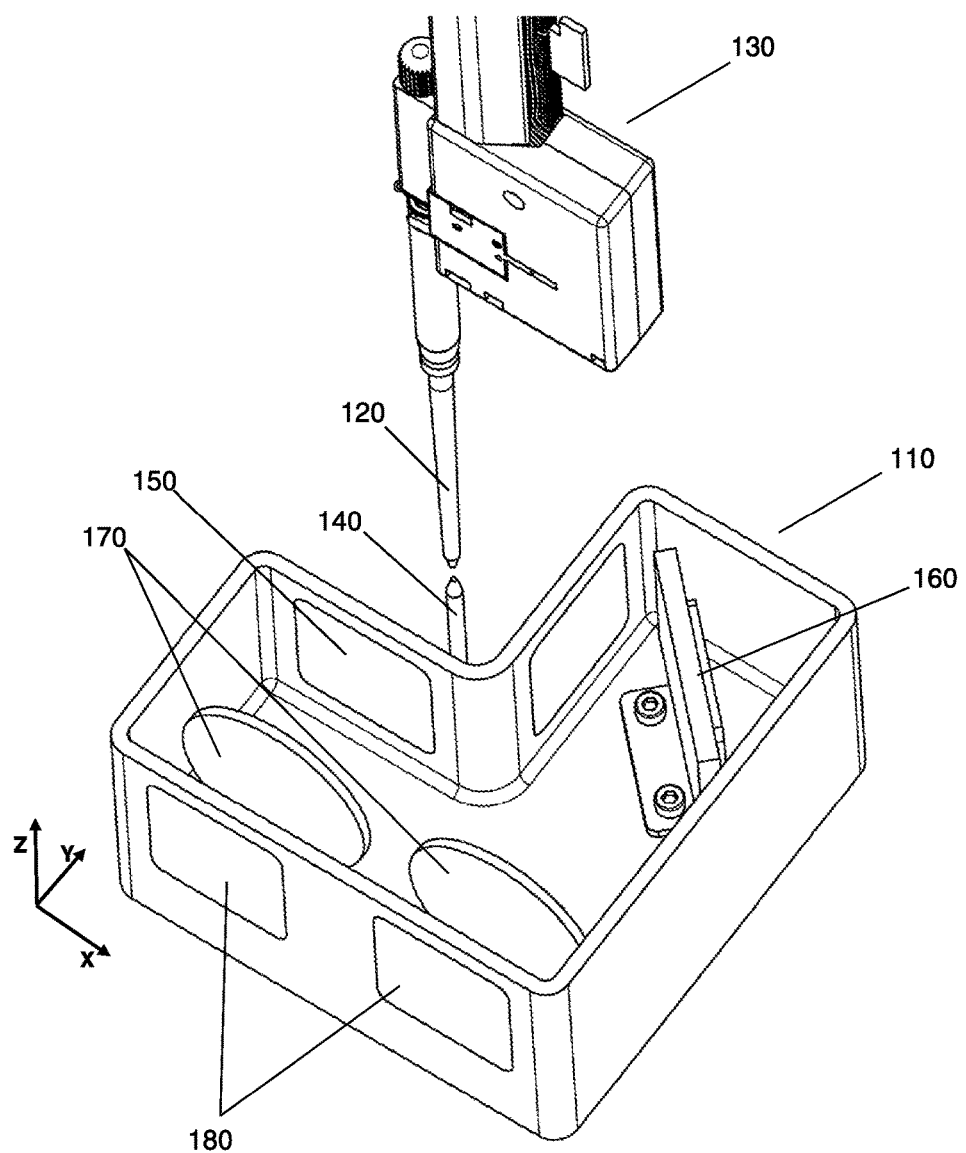
FIG. 1 shows a device of the present invention.

FIG. 1 discloses a device 110 according to the present invention. The device 110 is placed so that a pipettor tip 120 of a pipettor 130 and a reference point marker 140 at the base plate of an analyser system are visible in two first windows 150. The device comprises a mirror 160 and two lenses 170 inside the device. The two first windows 150 are perpendicular to each other, the mirror 160 is arranged behind one of the first two windows 150. The two lenses 170 are arranged behind two second windows 180. One of the first windows 150 and one of the second windows 180 are arranged parallel to each other, and one of the first windows 150 and one of the second windows 180 are arranged perpendicular to each other. The coordinate system showing the x-, y- and z-direction is shown at the bottom left for better orientation. The three coordinates are perpendicular to each other.

"Inside the device" means that the device is hollow so that lenses and mirror/s can be placed inside the device. The device thus comprises a body which incorporates the windows and a hollow inside which comprises the lenses and mirror/s.

The reference point marker indicates a reference position inside the analyser system. The lenses allow magnifying the visible pipettor tip and the visible reference point marker for easier alignment of pipettor tip and reference point marker.

The device is removable. It can thus be easily moved to any position within the analyser system to align a pipettor tip and a reference point marker.

The mirror is arranged such that a movement of the pipettor tip relative to the reference point marker is reflected, magnified by a lens and visible through a second window.

The terms pipettor tip and pipettor needle may be used synonymously.

The device allows easy and precise visual alignment of the pipettor tip and the reference point marker. Only one device is necessary to teach all reference point marker positions.

The device may be of any material. Hard materials, such as plastic or metal, are preferred over soft materials for better handling and stability.

Visual alignment has the purpose of aligning the pipettor tip and the reference point marker by determining the deviation of the position of the pipettor tip and the reference point marker in x-, y- and z-direction.

The use of mirrors and lenses ensures an easily visible pipettor tip and reference point marker, and the easy alignment of pipettor tip and reference point marker in all three dimensions.

The mirror, the lenses and the windows may be arranged in an L-shape as can be seen in FIG. 1. Different shapes are also possible. Two sides of the body of the device have to be perpendicular to one another so that both movements of the pipettor tip relative to the reference point marker (the movement in the xz-plane and the movement in the yz-plane) are visible.

The reference point marker can be pointed as shown in FIG. 1 but can also be flat or of a different shape. A pointed pipettor tip and pointed reference point marker allow easy alignment because the matching of the two positions can be easily visualized.

Figure 2:
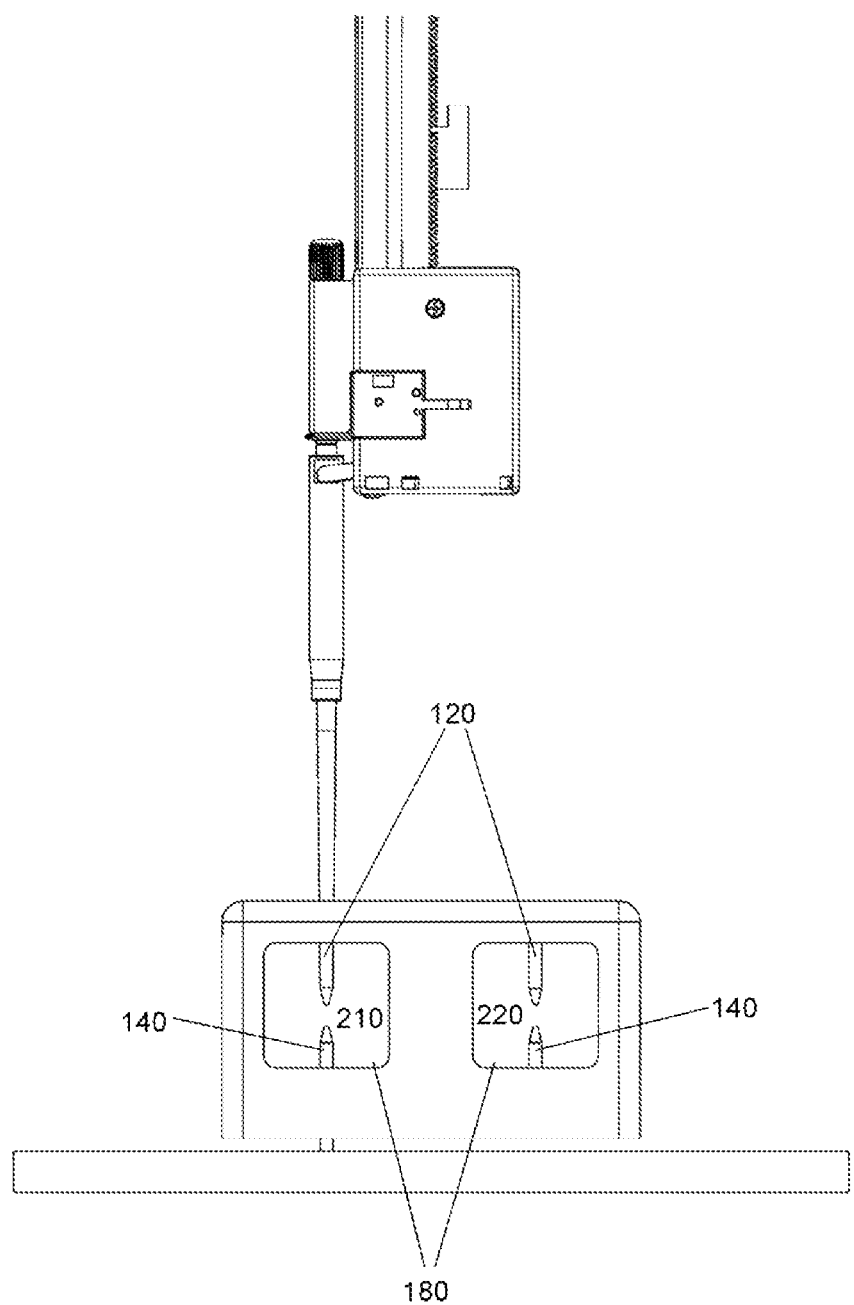
FIG. 2 shows a device of the present invention from a different perspective.

FIG. 2 shows the same device 110 as in FIG. 1, but from a different perspective. In the two second windows 180, the magnified pipettor tip 120 and magnified reference point marker 140 can be seen. The left window 210 of the two second windows 180 shows the movement of the pipettor tip 120 and the reference point marker 140 in the xz-plane. The right window 220 of the two second windows 180 shows the movement of the pipettor tip 120 and the reference point marker 140 in the yz-plane.

Windows of the device can be open, i. e. a recess within the body of the device, but they can also comprise a transparent material as long as the user can see the movement of the pipettor tip relative to the reference point marker through the windows.

It is to be understood that the device may also comprise more than four windows, more than two lenses and/or more than one mirror as long as the two movements (xz- and yz-plane) are magnified and visible. More than four windows shall mean that the device may comprise at least two first and at least two second windows but may also comprise one or two first windows and at least two or three second windows (and vice versa).

It is also possible that at least two windows are combined to a larger window so that the device comprises larger areas as windows. For example, two first windows can be combined to one window. This larger window may be bent so that two sides of this larger window are perpendicular to one another. Two second windows can also be combined. It is also possible that one first window and one second window is combined. Essentially, the device may even comprise one large window covering the whole side all around the body of the device. The terms "first window" and "second window" would in that case refer to the same window but to different parts of the same window.

Likewise, two lenses can also be combined to a larger lens. It is therefore not necessary that the two lenses are separate lenses as long as both movements of the pipettor tip relative to the reference point marker (in the xz-plane and in the yz-plane) can be magnified.

The present invention also relates to a system. The system comprises the device of the present invention and further a camera and a user interface. The user interface may be a computer monitor. The user interface is then used for visualization. The system may also comprise a camera and an instrument control unit.

A method for the visual alignment of a pipettor tip and a reference point marker in x-, y- and z-direction is also disclosed. The method comprises the following steps:
  placing the device of the present invention so that a pipettor tip and a reference point marker are visible in the two first windows,
  moving the pipettor tip relative to the reference point marker in a first movement in a xz-plane and magnifying the first movement by a lens so that the magnified first movement is visible through one of the second windows,
  moving the pipettor tip relative to the reference point marker in a second movement in a yz-plane, reflecting the second movement by a mirror, magnifying the reflected second movement by a lens so that the reflected magnified second movement is visible through another one of the second windows,
  aligning the position of the pipettor tip to the position of the reference point marker in x-, y- and z-direction.

Placing the device in the sense of the present invention means that the device is arranged within the analyser system so that visual alignment can be performed. The movement of the pipettor tip and the reference point marker may be a manual movement or an automatic movement.

The first movement may also be in the yz-plane and the second movement in the xz-plane. Thus, it is not definite which of the two movements is the first and the second movement. One of the movements is directly visible through a magnifying lens, while the other movement is first reflected by a mirror and then magnified by a lens for better visualization of the movement. The reflection by the mirror ensures that the user can see both movements from the same side of the device. Neither the device nor the user have to move for the both movements (xz-plane and yz-plane) to be visualized.

Figure 3:
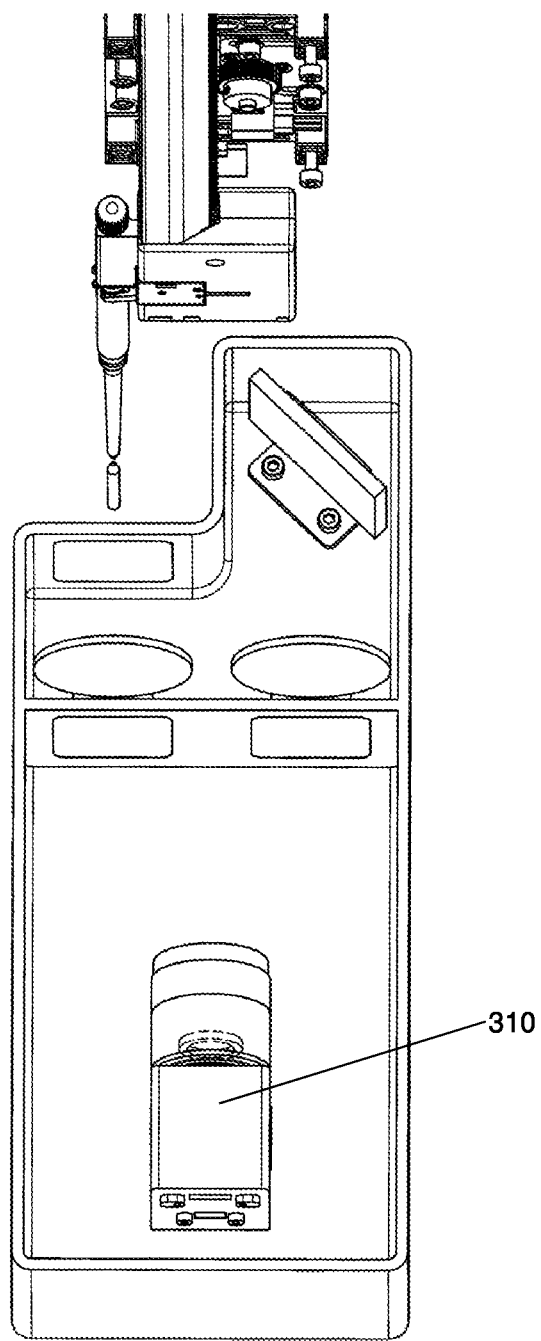
FIG. 3 shows a system of the present invention comprising a device of the present invention and a camera.

FIG. 3 showing a system of the present invention comprising a device of the present invention and a camera visualizes one embodiment of a system and method of the present invention, wherein a camera 310 acquires the first and the second movement. The first and the second movement may be visible on a user interface. The user interface may be a computer monitor so that the computer monitor is used for visualization of the alignment. Additionally or alternatively, the alignment is performed by an instrument control unit using image processing algorithms. Additionally means that the device is used together with a camera, a computer monitor and an instrument control unit so that the visualization on the computer monitor can be controlled and/or corrected by automatic alignment using image processing algorithms. Alternatively means that either a computer monitor is used for visualization or the alignment is done automatically by an instrument control unit using image processing algorithms. Using a camera together with the device thus allows an automated alignment. The automatic alignment is also considered a visual alignment in the sense of the present invention because the automatic alignment requires a camera for acquisition of the movement of the pipettor tip and of the reference point marker, thus the camera visualizes the movement.

The device of the present invention can be used for the visual alignment of a pipettor tip and a reference point marker in x-, y- and z-direction. The visual alignment is easy and precise.

The detection of the z position of the reference point marker may be supported by the use of pipettor integrated sensors, for example capacitive sensing when using an electrically grounded reference point marker or barometric pressure sensing when using a flat reference point marker top surface. In this case, the dispense pump of the analyser system generates an air stream out of the pipettor tip. When the pipettor tip is very close to the reference point marker the pressure inside the pipettor changes and thus the reference point marker's z-position can be detected.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS 110 device
120 pipettor tip
130 pipettor
140 reference point marker
150 first windows
160 mirror
170 lens
180 second windows
210 left window
220 right window
310 camera

What is claimed is:

1. A device for the visual alignment of a pipettor tip and a reference point marker in x-, y- and z-direction comprising:
two first windows that are arranged perpendicular in a plane to each other;
two second windows, which are arranged next to each other, wherein a first one of the first windows and a first one of the second windows are arranged opposite and parallel to each other, and a second one of the first windows is arranged perpendicular to both second windows;
a mirror that is arranged behind the second one of the two first windows; and
two lenses that are each arranged next to each other in a plane behind said two second windows; and
a reference point marker for the pipettor tip that is visible through said two first windows.

2. The device according to claim 1, wherein said mirror, said lenses and said two second windows are arranged in an L-shape.

3. The device according to claim 1, wherein two first windows or two second windows or one first window and one second window are each combined to one window.

4. The device according to claim 1, wherein two lenses are combined to one lens.

5. A system for the visual alignment of a pipettor tip and a reference point marker in x-, y- and z-direction comprising:
a device comprising:
two first windows that are arranged perpendicular to each other
two second windows, which are arranged next to each other in a plane, wherein a first one of the first windows and first one of the second windows are arranged opposite and parallel to each other, and a second one of the first windows is arranged perpendicular to both second windows;
a mirror that is arranged behind the second one of the two first windows;
two lenses that are each arranged next to each in a plane other behind said two second windows; and
a reference point marker for the pipettor tip that is visible through said two first windows;
a camera; and
a user interface.

6. The system according to claim 5, wherein the user interface is a computer monitor.

7. A system for the visual alignment of a pipettor tip and a reference point marker in x-, y- and z-direction comprising:
a device comprising:
two first windows that are perpendicular to each other
two second windows, which are arranged next to each other in a plane, wherein a first one of the first windows and a first one of the second windows are arranged opposite and parallel to each other, and a second one of the first windows is arranged perpendicular to both second windows;
a mirror that is arranged behind the second one of the two first windows;
two lenses that are each arranged next to each other in a plane behind said two second windows; and
a reference point marker for the pipettor tip that is visible through said two first windows;
a camera; and
an instrument control unit.

8. A method for the visual alignment of a pipettor tip and a reference point marker in x-, y- and z-direction, comprising the following steps:
providing a device comprising:
two first windows that are perpendicular to each other; and
two second windows, which are arranged next to each other in a plane, wherein a first one of the first windows and a first one of the second windows are arranged opposite and parallel to each other, and a second one of the first windows is arranged perpendicular to both second windows;
a mirror that is arranged behind the second one of the two first windows;
two lenses that are each arraigned next to each other in a plane behind said second windows; and
a reference point marker for the pipettor tip that is visible in the two first windows;

moving the pipettor tip relative to the reference point marker in a first movement in a xz-plane and magnifying the first movement by a lens so that the magnified first movement is visible through one of the second windows;

moving the pipettor tip relative to the reference point marker in a second movement in a yz-plane, reflecting the second movement by a mirror, magnifying the reflected second movement by a lens so that the reflected magnified second movement is visible through another one of the second windows; and aligning the position of the pipettor tip to the position of the reference point marker in x-, y- and z-direction.

9. The method according to claim 8, wherein the first movement is in the yz-plane and the second movement is in the xz-plane.

10. The method according to claim 8, wherein a camera acquires the first and the second movement and the first and the second movement are visible on a user interface.

11. The method according to claim 10, wherein the user interface is a computer monitor.

12. The method according to claim 8, wherein a camera acquires the first and the second movement and the alignment is performed by an instrument control unit using image processing algorithms.

* * * * *